Figure 1:
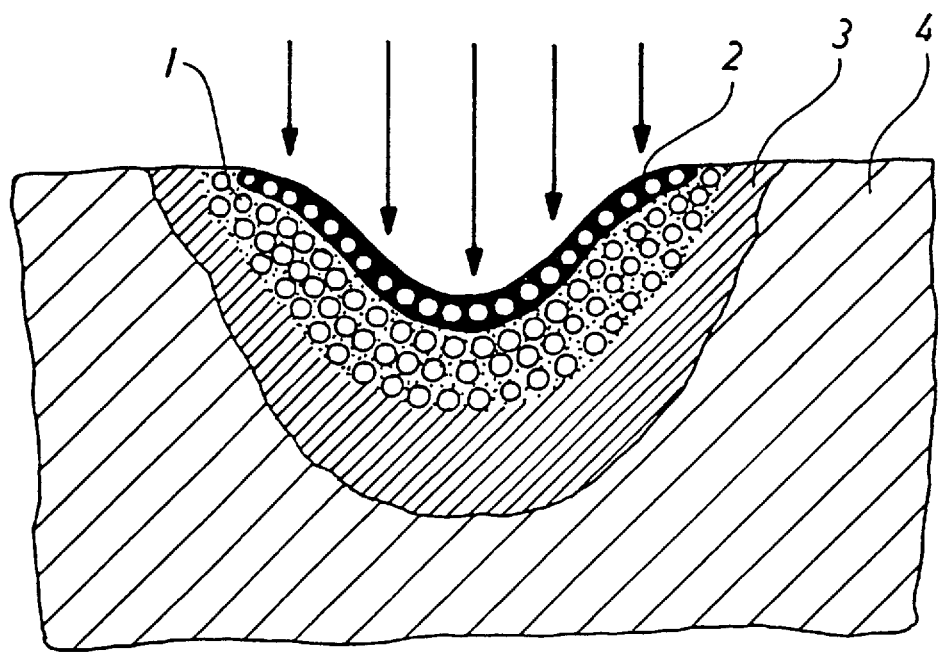

United States Patent [19]
Suslov

[11] Patent Number: 5,843,079
[45] Date of Patent: Dec. 1, 1998

[54] DEVICE TO STOP BLEEDING IN LIVING HUMAN AND ANIMAL TISSUE

[75] Inventor: Nikolai Suslov, Moskow, Russian Federation

[73] Assignee: Nikval International AB, Gothenburg, Sweden

[21] Appl. No.: 809,203

[22] PCT Filed: Aug. 29, 1994

[86] PCT No.: PCT/SE94/00790

§ 371 Date: May 20, 1997

§ 102(e) Date: May 20, 1997

[87] PCT Pub. No.: WO96/06572

PCT Pub. Date: Mar. 7, 1996

[51] Int. Cl.⁶ .................................................. A61B 17/36
[52] U.S. Cl. ............................................................ 606/43
[58] Field of Search ............................... 606/40, 49, 111; 607/101, 103, 104; 604/20, 21

[56] References Cited

U.S. PATENT DOCUMENTS

| | | |
|---|---|---|
| 3,991,764 | 11/1976 | Incropera et al. . |
| 4,788,408 | 11/1988 | Wlodarczyk et al. . |
| 4,855,563 | 8/1989 | Beresnev et al. . |
| 4,901,720 | 2/1990 | Bertrand ................................ 606/40 |

FOREIGN PATENT DOCUMENTS

92/19166  11/1992  WIPO .

*Primary Examiner*—William E. Kamm
*Attorney, Agent, or Firm*—IP Group of Pillsbury Madison & Sutro LLP

[57] ABSTRACT

An electrosurgical device employs a pencil-shaped instrument having a conductive tip formed of high melting point material such as zirconium or hafnium connected to the positive terminal of a high frequency generator and having a nozzle at the end for the passage of a gas from a supply to create a plasma at the nozzle end when placed on the patient to stop bleeding.

6 Claims, 7 Drawing Sheets

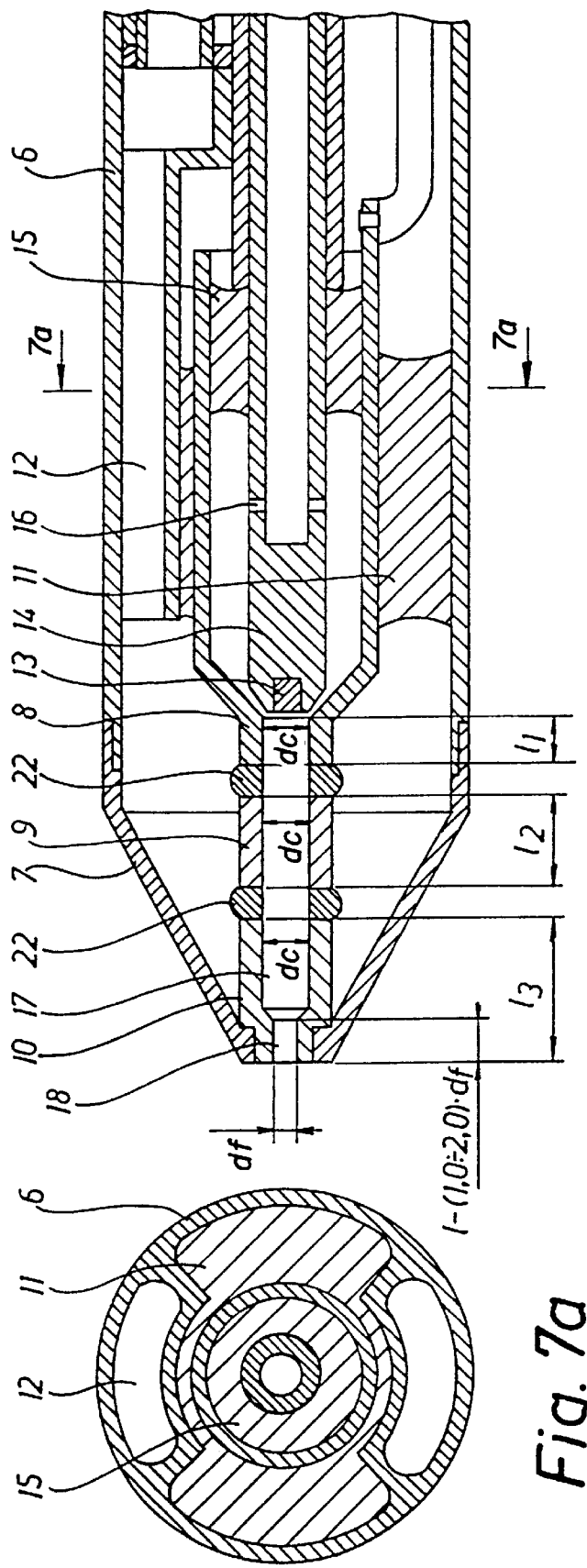

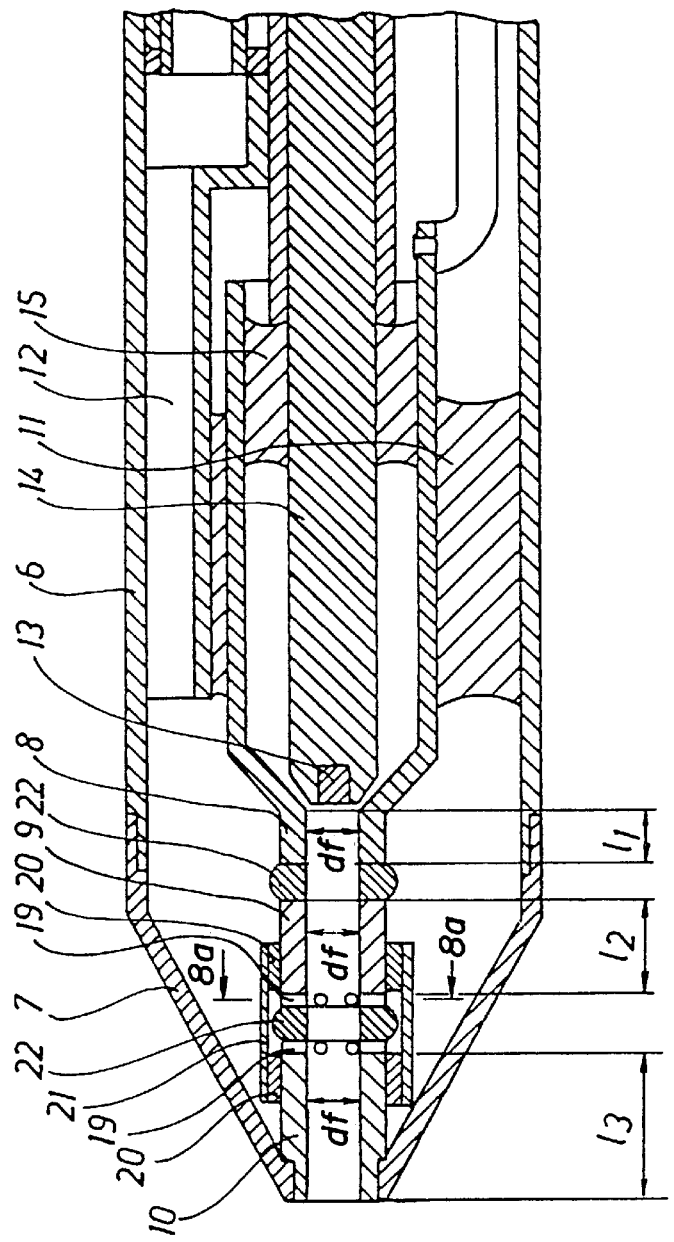
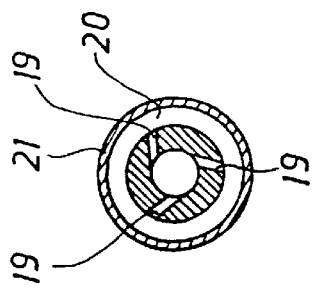
Fig. 8
Fig. 8a

DEVICE TO STOP BLEEDING IN LIVING HUMAN AND ANIMAL TISSUE

This application is the national phase of international application PCT/SE94/00790 filed Aug. 29, 1994 which designated the U.S.

The subject invention concerns a device to stop bleeding in live human and animal tissue and to form a crust by means of a plasma jet. The invention relates to plasma surgery and more particularly to a new and improved plasma surgical technique of achieving coagulation or a hemostatic effect, i.e. desiccation and coagulation by weak supply of plasma jet power to a layer of tissue and intense supply of jet power to the fluid component of the biological tissue.

The purpose of the invention resides in plasma dynamic desiccation of a surgical site and in the creation in said site of an area of thermal necrosis at a rate highly exceeding the rate of medium or intense bleeding with the aid of direct application of a plasma jet having definite thermo-dynamic characteristics.

Plasma flow, laser irradiation and electrosurgery are methods used in surgery for clean-cutting purposes, for combined cutting and hemostasis effect as well as for obtaining hemostasis of a surgical wound.

The dominant reactions induced by intense energy application on tissue are thermochemical in nature as a result of the energy absorption by the biological object. The major part of the energy is converted into heat.

The thermal effect of the application of an intense flow of energy explains the character of the biological processes developing in tissue during and after the application.

An analysis of the biological and hemostatic effect of a concentrated plasma flow and irradiation on tissue has shown that an area of thermal changes (ATC) is formed therein which comprises several zones. As a result of intense power supply the surface of the tissue is desiccated and a spongy desiccated necrosis layer is formed on the tissue surface. The surface of the spongy layer is carbonized—Carbonized Spongy Layer (CSL). Due to a conduction mode of heat transfer a compact necrosis layer (CNL) is formed This layer forms between the spongy layer and the unaffected liveg tissue. The generation of a compact necrosis layer is a result of the thermal denaturation of protein occurring as temperatures rise above 56° C.

From a medical-biological point of view the elimination of bleeding is obtained by creating an ATC and the level of hemostasis reliability depends on the size of the ATC and the time of its creation. In particular, the prior utilization of different methods of application (laser irradiation, plasma jet and electrosurgery) shows that positive hemostasis and lack of hazards during the healing process occur when the average thickness of the ATC is about 1.0 mm.

In the development work of the subject invention the characteristics of different layers in the area of thermal changes occurring when using conventional methods were carefully investigated.

Taking into consideration the bleeding rate when different necrosis layers were created in the area of thermal changes, fundamental disadvantages were found with respect to the various methods of thermal applications. Consequently, a need was felt for developing new methods for the purpose of achieving a high degree of efficiency in surgery on highly bleeding organs. Various such methods for creating characteristics of various zones of ATC will be discussed in the following.

While working on the prior technique emphasis has primarily been placed on the bleeding rate as a decisive factor when applying the method on high-rate bleeding organs. When the blood flow in tissue is heavy and the bleeding from a surgical incision is high, it is necessary to create an ATC ensuring that the vaporization rate of the liquid component is higher than the flow rate of the blood moving towards the incision. This means that the thermal energy developing inside the volume unit of the tissue as a result of the outer application must exceed the amount of power expended on vaporization of the volume unit of the blood flowing towards the incision.

To create a spongy desiccation layer on the surface of the tissue it is necessary to separate in space the boundary of sublimation of this layer from the boundary of vaporization of the liquid component. In this case it is moved towards the place of application at the speed of the blood flow rate, preventing the creation of a spongy necrosis layer.

Depending on the technique of energy supplied to the tissue different methods of application are available, among them methods of delivery of energy supply to the surface of a tissue where the tissue is heated and the creation of zones of necrosis in the ATC occurs at the expense of thermal conductivity. A method utilizing a $CO_2$-laser and a plasma jet belongs to this category. In order to obtain desiccation and create a spongy desiccation layer heat is in this case conducted to the boundary of vaporization of the liquid component by means of thermal conductivity. Because during the desiccation of tissue its thermal conductivity is reduced by 4–6 times compared with undesiccated tissue and by 0.62 W/m . °C., the rate of the displacement of the vaporization boundary with respect to the liquid component diminishes as well, which means that the rate of the ATC creation goes down considerably.

The use of this method allows the spongy necrosis layer to be obtained only during weak and rather moderate bleeding. This may be understood by the following example. In order to desiccate a layer of tissue during intense heating when an opposing blood flow is mov-ing at a rate of 2 mm/s, the thermal flow at the boundary of vaporization of the liquid component in the tissue must exceed $4.6 \times 10^6$ W/m². However, when the thickness of the desiccation layer is close to 0.25 mm the quantity of thermal flow at the boundary of liquid vaporization of the liquid component does not exceed $4 \times 10^5$ W/m².

This is due to the fact that the temperature of sublimation of the desiccated and charged surface is about 700° C. and the temperature of vaporization of the liquid component is about 100° C. This explains the difficulties of reducing and eliminating intense bleeding by using methods involving energy supply to a tissue surface. In particular, a plasma jet flowing along the tissue surface is not able to eliminate intense bleeding.

In accordance with another method energy is supplied to a tissue and allow to penetrate into it. In accordance with these methods a YAG (Nd-YAG) laser beam in the visible and the near-infrared region is used as well as electrosurgical application. In the first case, the energy is absorbed into the tissue to a depth of 1.0 mm. To achieve efficient desiccation of the tissue surface during the application of the laser beam the amount of thermal energy penetrating into the unit volume of tissue must slightly exceed the energy required to vaporize the blood flow in the tissue and the application must be terminated at the moment of achieving desiccation. This is essential in order to eliminate areas of heavy sublimation of the tissue surface, which would otherwise have led to destruction of the newly-constructed necrosis layer, as the desiccated layer have a much higher coeffecient of laser energy absorbtion than non-desiccated tissue. Intense sublimation of the desiccated layer results if the application is continued after the formation of a spongy layer. This feature is one of the most essential drawbacks connected with the use of laser radiation within the visible and near-infrared regions in order to eliminate medium and heavy bleeding.

In the second case the energy supply to the tissue is effected by application of high-frequency current to the tissue. As soon as desiccation is achieved, its impedence increases considerably, resulting in termination of the application and the achievement of a desiccated layer.

The most efficient method of eliminating heavy bleeding is to make use of the electrosurgical technique in order to obtain coagulation, which is described in the U.S. Pat. No. 4,781,175.

This publication concerns conducting a predetermined ionizable gas in the form of a jet to the tissue as the predetermined flow rate that is sufficient to clear the tissue of natural fluids and to expose the connective tissue (stroma) to an essential degree. Electric radio frequency energy is conducted to the tissue in ionized conductive pathways in the gas jet. To achieve fulguration, the electrical energy is conducted in the form of arcs in ionized conductive pathways. To achieve a non-contact type of electrosurgical desiccation, the electric energy is conducted as a non-arcing diffused current in the ionized conductive pathways.

The conduction of energy into the bulk of the tissue is pointed out the be one of the advantages of the described method, providing a rapid build-up of a desiccation layer on the surface of intense-bleeding surgical incisions.

The use of a laminar jet of an inert gas in order to remove blood from the surgical site and also for substantially uniform distribution of electric power within the tissue makes it possible to create thermally desiccated layers having a uniform depth compared with prior art electrosurgical techniques.

In addition, this method involves feedback during the application because the energy supply stops at the moment of tissue surface desiccation, i.e. after the final creation of the spongy necrosis layer. This deminishes the generally harmful effect of the method and provides an opportunity to chose determined regimes with guaranteed power amounts and hence with guaranteed achievement of arresting intensive bleeding.

The main disadvantages of electrosurgical application on biological tissue are the following. In order to stop intensive bleeding it is necessary to increase the amount of energy of the application, which is carried out at the expense of the regime of the microarc generation between the tissue and the surgical instrument. The emission of energy in biological tissue involves passing current through a patient, which may limit its usage (for instance in the case of heart diseases). This method does not allow precise incision to be made in tissue in contrast to the characteristics of the laser beam method.

Traditional plasma methods are characterized by a supply of thermal energy to a tissue surface by means of a plasma flow, which makes it rather difficult to use it in connection with medium and intensive bleeding. The disadvantages of plasma application may be eliminated only by heat exchange between the plasma flow and the biological tissue.

The invention provides a device to stop bleeding in live human and animal tissue by means of which the disadvantages found in prior-art devices of various kinds have been eliminated. The principal characteristics of the device appear from the appended claim 1.

Figure 2:
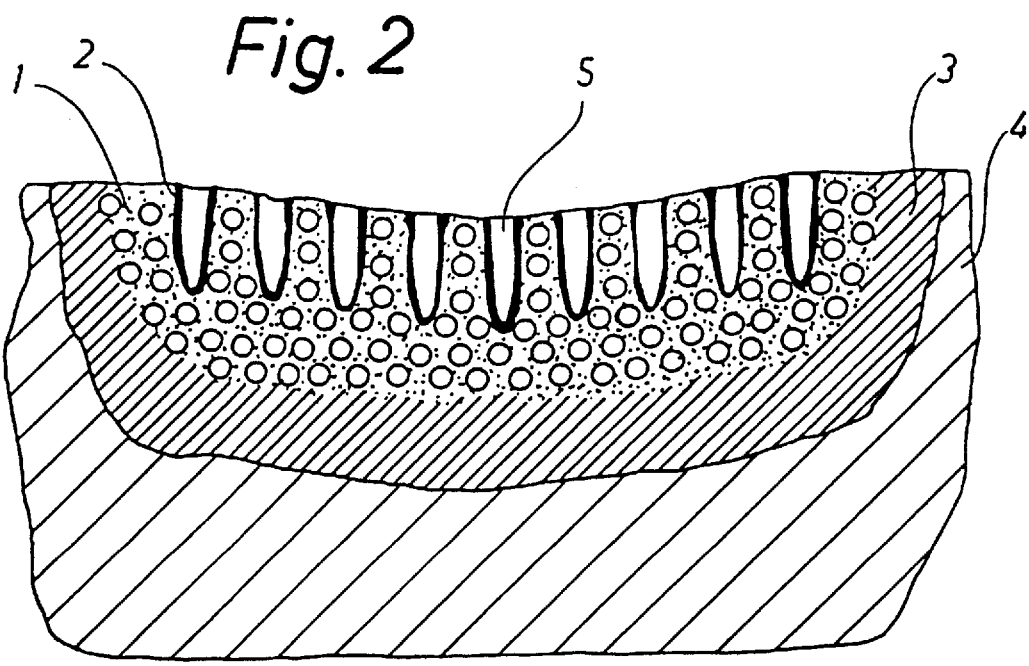
Figure 3A:
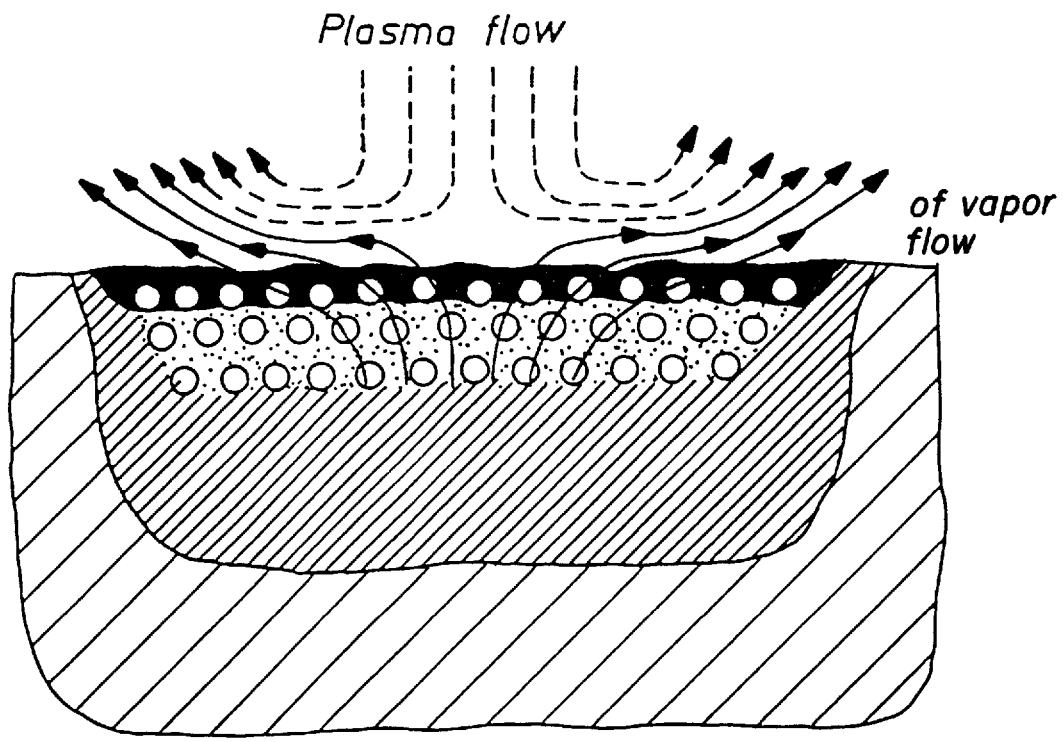
Figure 4:
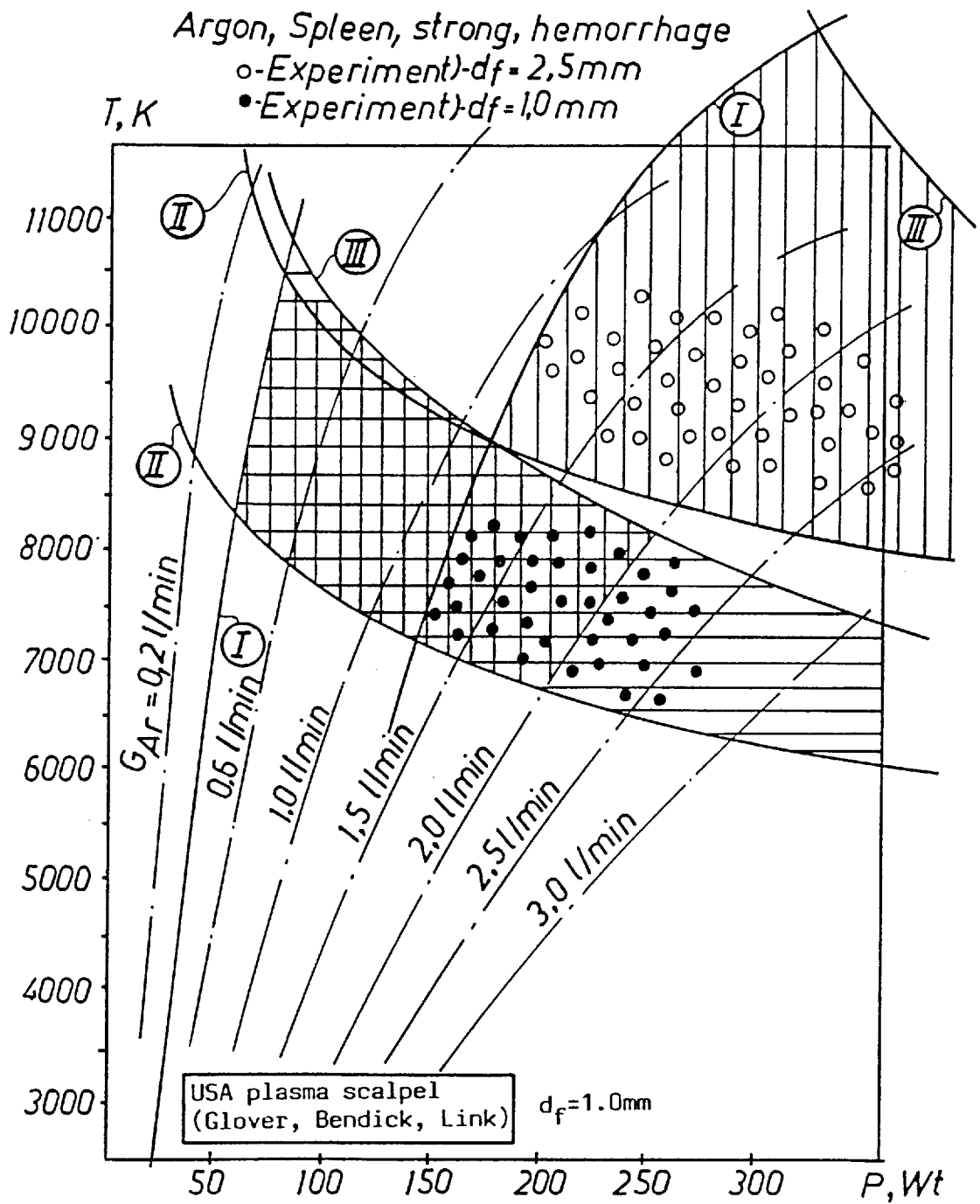
Figure 5:
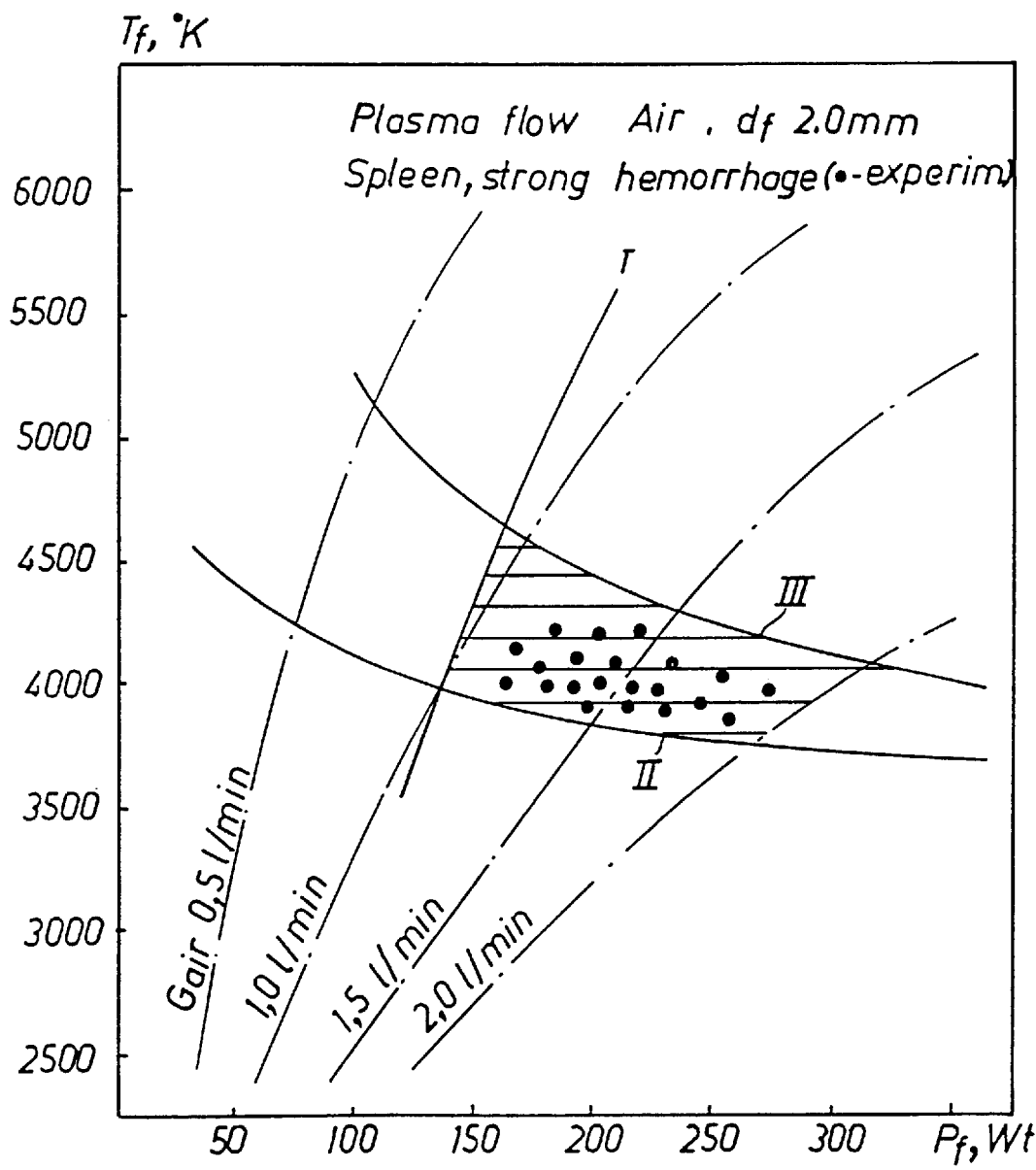
Figure 6:
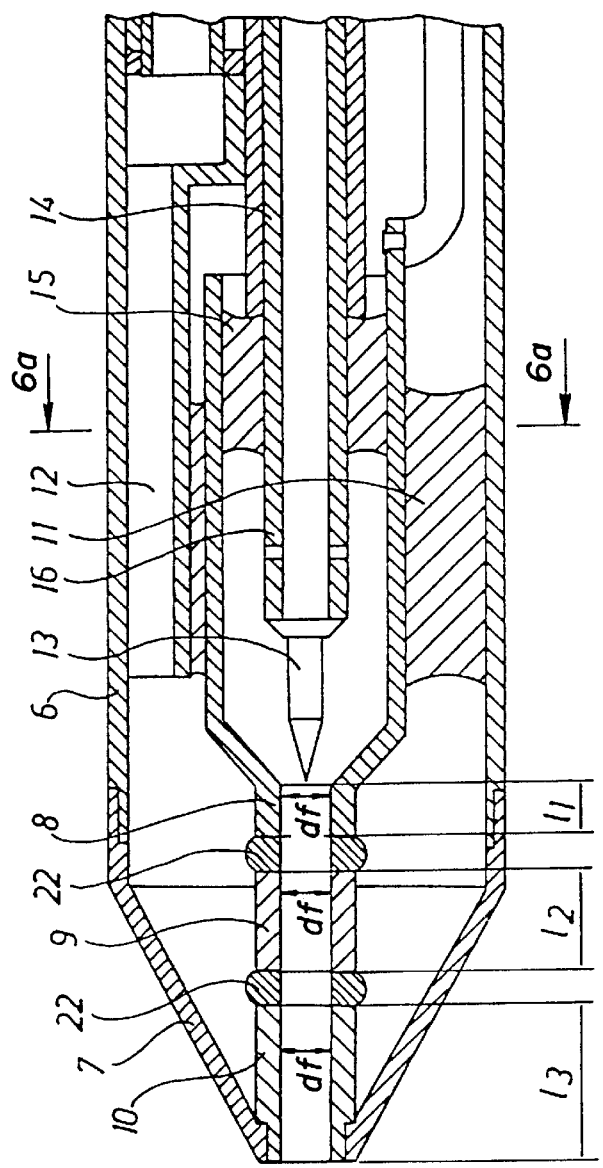
Figure 6A:
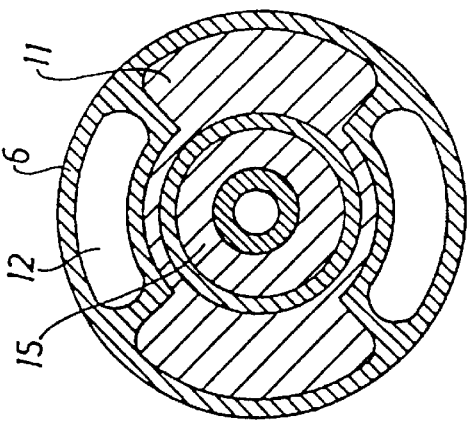

The invention will be described in closer detail with reference to the accompanying drawings wherein FIG. 1 is a cross-sectional view through a wound in tissue that has been treated by means of the device in accordance with the invention, FIG. 2 is a corresponding cross-sectional view through tissue treated by means of an electrosurgical method, FIGS. 3a and b are corresponding sectional views schematically illustrating the inter-active flows to and away from a tissue, FIGS. 4 and 5 shows coordinate systems with curves representing measured values of thermal energy as a function of plasma jet temperatures, FIG. 6 is longitudinal sectional view through a plasma nozzle in accordance with one embodiment of the invention wherein an inert gas is used, FIG. 6a is a cross-sectional view along line A—A in FIG. 6, FIGS. 7 and 7a are corresponding sectional views but show a different embodiment of the plasma nozzle wherein the used gas is air and FIGS. 8 and 8a are corresponding sectional views of a third embodiment of the plasma nozzle using water vapor.

FIG. 1 is sectional view through a treated wound in a tissue. Numeral reference 1 designates a spongy desiccated layer showing locally dead cells (necrosis). This layer 1 is covered by a carbonized layer 2. Owing to heat transfer a compact necrosis layer 3 has formed underneath the spongy desiccated layer 1. The necrosis layer is formed between the spongy layer 1 and the unaffected, live tissue 4.

FIG. 2 shows a wound treated with the aid of electrosurgical technique. In this case the spongy layer 1 is characterized by an external, essentially uniform-depth supporting tissue (reticulum) having holes 5 created by means of a light arc. The holes are essentially of identical cross-sectional area and are essentially evenly distributed across the eschar surface. The tissue intermediate adjacent holes 5 confers pliability to the eschar, preventing cracking. And generally uniform-depth thermally desiccated layer 3 separates the arc hole reticulum from the unaffected tissue.

The high porosity of the necrosis layer (as will be shown below it amounts to approximately the percentage of fluid component in the tissue −75–85%) makes it possible to use the essentially novel method of plasma flow to obtain this layer under extensive bleeding conditions.

As mentioned above the difficulties of arresting intense bleeding are related to the need for separating in space the external boundary of tissue surface sublimation and for presenting in the depth of the tissue the boundary of fluid-component vaporization. The latter boundary moves with blood flow rates towards the application and prevents the formation of a spongy necrosis layer, in particular in the case of intense bleeding.

Figure 3B:
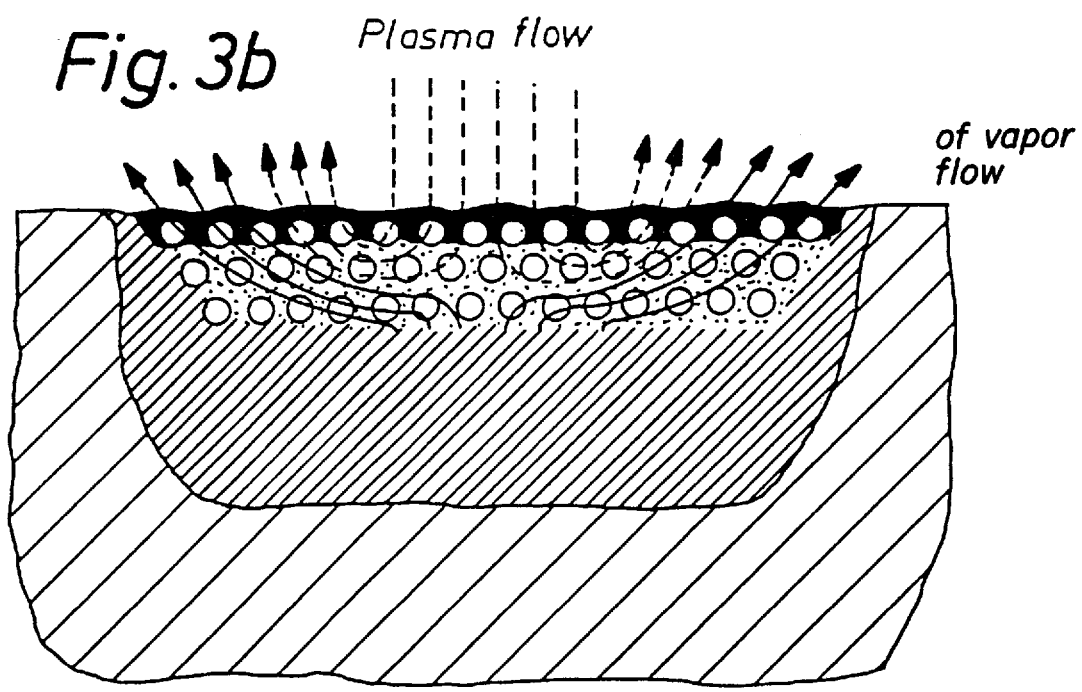

The presence of various forms of energy resources is typical of plasma jet. The plasma flow energy is concentrated as a form of plasma enthalpi, a dynamic component of jet energy and broadband emission of ionized gas. By changing the consumption of the plasma-generating gas, the cross-sectional area of the plasma jet and its temperature it becomes possible to control the dynamic pressure of the plasma flow. Consequently, it becomes possible to establish interaction between the plasma jet and the spongy necrosis layer when the plasma jet penetrates this layer completely or partly. As a result, the plasma jet is partly cooled while heating the spongy necrosis layer and the remaining part of the jet energy is absorbed at the boundary of the vaporization of the tissue fluid component. The filtration of the cooled plasma-generating gas and of the vapour flow takes place through the low pressure area of the plasma jet. The above-described modes of interactions between the plasma jet and the tissue surface are shown schematically in FIG. 3.

This analysis points out a new principal possibility of conducting energy to tissues by making use of a plasma-dynamic effect of a ionized gas flow. The high porosity of the spongy necrosis layer established by predetermined thermo-physical and gasodynamical parameters in the plasma flow results in gasodynamical and thermal penetration by the plasma jet in this layer 3b. In this case it becomes possible to realiae combined properties in the conduction of energy to tissue—volume power delivery to the spongy necrosis layer and superficial heating of the fluid component of the tissue within the spongy layer.

The investigation of the porosity of the spongy layer has indicated that the cross-section of pores d and the porosity P with respect to typical parenchymatous organs are: lungs d=0.06–0.09 mm, P=0.9–0.95, spleen d=0.04–0.07 mm, P=0.85–0.9, liver d=0.035–0.06 mm, P=0.75–0.8, kidney d=0.02–0.04 mm, P=0.65–0.7. As a result, the maximum cross-section of a plasma jet that realizes penetration of plasma flow in the spongy necrosis layer to a depth of about 0.25 mm equals 3.5 mm in lungs, 3.0 mm in the spleen, 2.5 mm in the liver and 1.5 mm in kidneys.

These data are applicable to an argon plasma jet. The use of lighter gases (neon, air and helium) leads to a reduction of the tolerable jet cross-section.

In order to establish the influence of plasma-generating gas parameters on the efficiency of arresting intensive bleeding investigations have been carried out on arrests of bleeding in experimental subjects (53 dogs in more than 500 experiments). The dogs were anesthezed and regional resections were carried out. The area of the wound surface was within 3–14 cm$^2$. Before the coagulation of the wound surface started the value of wound bleeding was measured at a fixed time as also the wound area and from the results it became possible to calculate the mean flow-rate of blood from the wound and to define the intensity of the bleeding.

The mean bleeding rate from a liver wound lay within the area of 0.6–1.8 mm/s, from a spleen wound 0.8–2.5 mm/s. It should be pointed out that intensive bleeding corresponds to an average bleeding rate of U>1.0 mm/s.

In accordance therewith various sources of action were compared with each other, possessing bleeding rates of 1.5–2.0 mm/s. In the investigations using microplasmatrons working on helium, neon, argon, nitrogen and air, the plasma flow parameters could be changed within a wide range since these microplasmatrons were produced without taking into consideration some limitations required for the surgical plasma generators, in particular the following: small dimensions, convenience of manipulation and handling, stability and reliability, major overhauls, minimum content of erosion products on the electrodes, limited gas consumption to exclude of gaseous embolism and some other limitations.

The results of these investigations are shown in FIGS. 4 and 5. The black dots correspond to the values of the thermal power and plasma jet temperatures that provide reliable arrest of intensive bleeding. Lines I, II, III illustrate the parameters of the plasma jet boundaries beyond which it was not possible to stop bleeding.

When helium was used it was possible to achieve reliable arrest of bleeding only at a bleeding rate of U≦1.0 mm/s.

These findings give evidence of a principal effect of the plasma-generating gas and of the thermo-physical properties of plasma. Particularly helium plasma fails to provide arrest of intensive bleeding in practically every range. By using argon, neon and air it becomes possible to stop intensive bleeding but their use involves limitations of the thermo-physical parameters of the plasma flow, of the extent of consumption of the plasma-generating gas and of the plasma jet cross-sectional area.

To analyze the particularities of these limitations a numerical model of interaction between plasma flow and live tissue has been developed. This model comprises:

percentage of fluid component in the tissue bleeding rate from wound volume density of blood flow in the tissue distinction of the thermo-physical characteristics of the tissue upon phase-structural changes and the formation of ATC distinction between temperatures of vaporization of the liquid component of the tissue and of the sublimation of the charring spongy layer gasodynamics of plasma jet flow and vapour flow in the spongy necrosis layer.

The analysis of experimental data and the realization of a numeric model show that the existence of limitations with respect to the plasma flow parameters that reliably arrest intensive bleeding is determined by the following principal characteristics of interaction between the plasma jet and the live tissue.

1. Boundary line I defines the condition of gasodynamic penetration of the plasma flow into a porous dessicated tissue layer, to a depth of 0.2–0.25 mm, i.e. exceeding by 3–5 times the a characteristic cross-section of the pores d. The position of the boundary I is determined by tissue species and depends on the cross-sectional area of the plasma jet.

2. Boundary line II defines the condition of vaporization of the liquid component of the tissue at a rate exceeding the rate of bleeding. The position of boundary II is determined by the extent of cooling of the plasma jet in the bulk of the spongy necrosis layer and is defined by the parameter $$\frac{\lambda_f \cdot P}{C_{pf} \cdot \mu_f \cdot d}$$

i.e. the type of the plasma generating gas. An analysis of the investigation of the heat transfer process in the porous systems in which gas flows shows that the intensity of the heat transfer in the pores is determined by $$\frac{\lambda_f}{C_{pf} \cdot \mu_f} < 2.0$$

This in turn explains the dependence of the creation of a spongy dessicated layer on the thermo-physical characteristics of the plasma flow obtained during experiment.

3. Boundary line III defines the condition of intensive sublimation of a carbonized spongy layer when the boundary of tissue sublimation coincides with the boundary of the fluid component. Besides the limitations mentioned it is necessary to also take into account that the very considerable volume increase of the plasma-generating gas consumption may be the cause of the generation of gaseous embolism. Investigations show that in order to exclude gaseous embolism appearance the value of argan and air consumption must not exceed 2.0 l/min. To increase the temperature of the argon plasma jet to a value above 10 500° K it is necessary to increase the discharge current rate to more than 30 A, which leads to the appearance of intensive erosion of the electrodes and to the occurrence of erosion products in the field of operation. Considering these factors the parameters most suitable for arresting intensive bleeding by means of a plasma jet are those falling within the marked areas.

The results from the investigation prove that the arrest of intensive bleeding as a result of plasma application takes place within a limited area of thermo-physical characteristics and of gasodynamic parameters of the plasma jet. In addition, it does not provide a reliable arrest of intensive bleeding when plasma-generating gases are used that have high heat conduction, low heating capacity and low viscosity.

The gas providing the widest range of change of the plasma parameters and able to arrest heavy bleeding is argon. The use of air as the plasma generating gas could also make it possible to stop intensive bleeding but within a much narrower range of plasma parameters compared with argon. It should be noted that in order to generate plasma flows having the above-mentioned parameters some limitations of the plasma surgical instrument must be respected. In particular, surgical microplasmatrons must generate plasma flows having an average mass temperature valid for the given type of gas (argon or air) of a necessarily comparatively high value (argon 7500–10 500° K, air 4500–5000° K) and that must change only insignificantly during fluctuations of consumption of the plasma-generating gas (between the limits 1.0–2.0 l/min). Furthermore, the above parameters of plasma flow must be achieved with limitation of the value of the discharge current at a level near 30 A, excluding erosion of the electrodes of the microplasmatron.

In order to obtain a guaranteed hemostatic effect in the wound surface during a significant change of the bleeding intensity it is necessary that the plasma-surgical instrument generates a plasma jet at a stable and comparatively high level of its temperature. The jet temperature must not change significantly during the regulation of the consumption of the plasma-generating gas. To attain high-level plasma flow temperature it is necessary to diminish the cross-section size of the electric arc that heats the gas. This means that the chamber channel for heating the plasma-generating gas by means of an electric arc must have a reduced cross-sectional size.

Proceeding from the required level of gas consumption (1.0–2.0 l/min) and taking into consideration the elimination of its thermal choking during heating the minimum cross-sectional area of the chamber channel for heating the plasma-generating gas must be 0.5 mm and according to the investigation the optimal size thereof falls within the range of 0.7–1.0 mm in the case of air and 1.0–1.5 mm in the case of argon.

This cross-section of the electrical arc results in a high value of the electrical field strength in the channel and the length of the channel that is necessary to heat the argon at the consumption rate of 2.0 l/min is insufficient to provide the electric discharge-distance strength. In this case a voltage drop in the plasma of the electric arc increases above 15–16 V (total value of voltage step input) and in consequence thereof instead of one long arc two sequential arcs appear, burning at a lower voltage and not providing gas heating to a high temperature.

To exclude electric breakdowns in the channel designated to heat the plasma-generating gas this channel is designed as electrically isolated sections. Its number must not be less than three. The highest electrical field strength is generated by the initial field of the electric arc at the cathode where a cooled gas enters into the arc. The length of the channel sections must be increased at a distance from the cathode since the field strength decreases. The most suitable channel geometry is to design it with a length of its first section at the cathode equalling its cross-sectional dimensions ($l_1=d_c$) with the length of each subsequent section being $l_n=n.d_c$ where n represents the number of sections. The sections are interconnected via non-electrically conductively gaskets. The first channel section is connected to the positive pole of a pulse periodic energy accumulator and to a high-voltage spark gap (triggering system of a surgical microplasmatron).

The last section is connected to the positive pole of a main power source in the surgical microplasmatron. A suitable length of this section is two to three times the diameter of channel d. All channel sections with the exception of the last one have the same cross-sectional dimensions. The last section should, for the purpose of dissecting tissues in optimal modes of operations, have a channel width of 0.4–0.6 mm. Its design when employed for this purpose does not depend on the kind of plasma-generating gas used.

When a microplasmatron is used to stop bleeding from a wound surface the cross-sectional size of the last channel section does, however, depend on both tissue species and type of plasma-generating gas.

When argon gas is used to stop bleeding from surgical incisions on the lungs, the spleen and the liver the cross-sectional dimensions of the last channel sections should be 2.5 mm and in the case of kidneys 1.5 mm.

In FIG. 6 a basic embodiment of a plasma surgical unit is shown, consisting of an electrically conductive body 6 similar to a pencil with a tip 7 for forming a plasma jet having the required cross-section and connected to a positive pole of a gas power source having a positive potential. The body 6 comprises a cylindrical channel to heating the plasma-generating gas and it is formed from channel sections 8, 9, 10 which are electrically isolated from each other and which are connected to the body 6 through an electrically isolated concentric bush 11 having channels 12 for conveyance of cooling fluid to and from the gas heat-ing channel. The sections 8, 9, 10 are interconnected by means of non-electrically conductive sleeves 22.

Sections 8, 9 but not section 10 have an equal cross-section $d_c$ and the same channel length $l_n$, n being the number of sections as calculated from the cathode 13. The total number of these sections must not be less than three and the length of each subsequent section separated from the cathode must be $l_n=n.d_c$.

The last section 10 which is designed to form the plasma jet, is connected with the tip 7 and has a channel cross-section $d_f$ to stop bleedings from large surgical wounds. The cross-section depends on the kind of plasma-generating gas and the species of the biological tissue.

To dissect biological tissues the channel of section 10 is constructed as two co-axial cylindrical holes 17, 18 (see FIG. 7) having an entrance diameter identical to the diameter of all precedings sections $d_c$ and an exit hole 18 having the diameter $d_f=0.4$–$0.6$ mm and the length $l=(1.5$–$2.0).d_f$.

The first section 8 is configured as a hollow cylindrical electrode which is connected with the body 6 via the electrically isolated bush 11 and with the cathode 13, 14 via the electrically isolated sealing bush 15. The sections are mutually interconnected via electrically insulated gaskets 22.

The cathode consists of an electrically conductive tube 14 on one end of which the electrode 13 from a high-melting metal is fixed, providing the required level of current for thermal-electronic emission within the working range of discharged currents. The opposite end of the tube serves as a connection to the gas supply unit and is connected with the negative poles of the basic energy source and of the trigger system of the microplasmatron. The electrically conductive tube 14 is formed with holes 16 for input and uniform distribution of the plasma-generating gas to the discharge chamber of the microplasmatron.

In order to work with inert a plasma-generating gases (argon, crypton, xenon) the electrode of the cathode 13 is made from wolfram or its alloys. In order to use air or steam as the plasma-generating gas the electrode of the cathode 13 is made from zirconium or hafnium (FIGS. 7, 8).

When steam is used as the plasma-generating gas the second last and the last sections 9 and 10, respectively, are formed at the beginning and the end, respectively, with tangentially positioned channels 19 (see FIG. 8) which are connected to the channel heating the plasma-generating gas and having the volume separated from the cooling water by means of inserts 20 formed with pores positioned inside a heat insulated cylindrical sleeve 21. The porous inserts 20 cover at least half of the external surface of the second last and the last sections 9 and 10. The water-filled cavity is connected to a system regulating the water pressure in order to control the quantity of steam consumption. The discharge current provides the required temperature of the plasma flows and the size of the steam consumption is between 3.0 and 8.0 A.

It should be obvious that the eschar resulting from the use of the device proposed in accordance with the subject invention has a well defined spongy necrosis layer having a thickness of 0.15–0.25 mm, which corresponds to between 3 and 5 characteristic cross-sections of pores therein.

The porous layer in accordance with the invention has a well defined boundary towards the subjacent tissue, which indicates the highly restricted heat penetration into the tissue and the localisation in this area of the boundary of vaporization of the liquid component of the tissue.

A comparison of the thickness of the spongy necrosis layer (SNL) resulting from the exposure to plasma and laser on liver and spleen wounds with intensive bleeding shows that in the first case the SNL has a thickness which is between 3 and 5 times larger than in the second case.

The pore size upon plasma exposure is 1.5 times less that upon laser exposure and the thickness of tissue intermediate the pores is 1.3 times larger. This indicates that the permiability of a spongy dessicated layer is approximately similar to that of a dessicated tissue obtained by means of methods involving slow heating at a temperature which only slightly exceeds that of vaporization of the tissue liquid component of the tissue.

These investigations of the reparative processes in the tissue of liver, lungs and kidneys have shown that the healing after the exposure to argon, neon and helium plasma flows takes place in the conventional way and is not dependent on the type of gas used. The healing of organs takes place without deformation of rough scars therein.

The device in accordance with the invention is not limited to the features shown and described but could be varied in several ways within the scope of the appended claims.

I claim:

1. A device to stop bleeding in live human and animal tissue and to form an escarre by means of a plasma jet, characterized in that the device comprises means for the generation of plasma, comprising an electrically conductive body (6) having the appearance of a pencil and formed with a tip (7) for forming the required cross-section of the plasma jet, said body (6) being connected to a positive pole of a gas power source having a positive potential, the body (6) comprises a cylindrical channel (17) for heating the plasma-generating gas, said channel being formed from a number of sections (8, 9, 10) which are electrically insulated from each other and each one of which is connected to the body (6) via electrically insulated bushes (22) which are concentric with the sections (8, 9, 10) and which are formed with channels (19) designed to conduct cooling liquid to and from the gas-heating channel (17), said sections (8, 9, 10), except the outermost one (10), having an equal channel cross-section $d_c$ and the same channel length $l_n$, n being the number of sections calculated from the cathode (13, 14), the number of said sections having to be at least three in addition to which the length of each subsequent section, separated from the cathode (13), must amount to $l_n = n \cdot d_c$, the outermost section (10), which is arranged to shape the plasma jet, is connected with the tip portion (7) of the body (6) and, in order to stop bleeding from surgical wounds, has a channel cross-section equalling $d_f$ determined by the kind of plasma-generating gas and the species of the biological tissue, said channel, in order to dissect biological tissue, being shaped as two co-axial cylindrical bores (17, 18) the entrance cross-section of which equals the cross-section $d_c$ of all preceding sections (8, 9) and the cross-section $d_f$ at the exit of which equals 0.4–0.6 mm and the length l of which equals $(1.5–2.0) \times d_f$.

2. A device as claimed in claim 1, characterized in that the innermost section (8) is in the form of a hollow cylindrical electrode which is connected to the body (6) by way of an electrically insulated bush (11), and comprises the cathode (13, 14) which is connected to the section (8) through an electrically insulated sealing gasket (15).

3. A device as claimed in claim 1, characterized in that the cathode (13, 14) is an electrically conductive tube (14) to one end of which a high-melting metal electrode (13) is attached, said electrode arranged to provide the required current level upon thermo-electronic emission within the operative range of the discharge currents, and in that the opposite end of said tube (14) serves as the connection for gas transportation and for the negative pole of the base energy source and the negative pole of the trigger system of the microplasmatron, and in that the electrically conductive tube (14) is formed with holes (16) to convey and evenly distribute the plasma-generating gas into the flow chamber of said microplasmatron.

4. A device as claimed in claim 2, characterized in that the electrode (13) of the cathode (13, 14) is made from wolfram or its alloys.

5. A device as claimed in claim 2, wherein air is used as the plasma-generating gas, characterized in that the electrode (13) of the cathode (13, 14) is made from zirconium or hafnium.

6. A device as claimed in claim 1, wherein steam is used as the plasma-generating gas, characterized in that the second outermost and the outermost sections (9, 10) are formed at their front and rear parts with tangentially positioned channels (19) which are connected to the channel (12) for heating the plasma-generating gas and having the space separated from the cooling water by means of porous inserts disposed in a thermo-insulating cylindrical bushing (21), and in that said porous inserts cover at least half of the outer surface of the second outermost and the outermost sections (9, 10).

* * * * *